US010712325B2

(12) United States Patent
Lejeune et al.

(10) Patent No.: US 10,712,325 B2
(45) Date of Patent: Jul. 14, 2020

(54) METHOD AND APPARATUS FOR MEASURING INFLORESCENCE, SEED AND/OR SEED YIELD PHENOTYPE

(71) Applicant: BASF PLANT SCIENCE COMPANY GMBH, Ludwigshafen (DE)

(72) Inventors: Pierre Lejeune, Tilff (BE); Jeroen Baert, Erpe-Mere (BE); Frederik Leyns, Oosterzele (BE); Joris Eeckhout, Maarkedal (BE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

(21) Appl. No.: 16/515,307

(22) Filed: Jul. 18, 2019

(65) Prior Publication Data
US 2019/0346419 A1    Nov. 14, 2019

Related U.S. Application Data

(62) Division of application No. 16/060,081, filed as application No. PCT/EP2016/079952 on Dec. 6, 2016, now Pat. No. 10,393,719.
(Continued)

(30) Foreign Application Priority Data

Dec. 10, 2015  (EP) ..................... 15199373

(51) Int. Cl.
*G01J 3/40*       (2006.01)
*G01N 33/00*    (2006.01)
(Continued)

(52) U.S. Cl.
CPC ..... *G01N 33/0098* (2013.01); *G01N 15/1429* (2013.01); *G01N 15/1434* (2013.01);
(Continued)

(58) Field of Classification Search
CPC ........ G01J 3/02; G01J 3/14; G01J 3/28; G01J 3/40; G01N 21/31
(Continued)

(56) References Cited

U.S. PATENT DOCUMENTS 5,058,369 A * 10/1991 Garner .................. A01D 23/04
                                                                 56/126
2004/0017761 A1 * 1/2004 Aoyama .............. G02B 5/3083
                                                                 369/112.17
(Continued)

FOREIGN PATENT DOCUMENTS

EP    1332354 A2    8/2003
EP    1431744 A1    6/2004
WO    WO-98/14046 A1    4/1998

OTHER PUBLICATIONS

Crowell et al., High-Resolution Inflorescence Phenotyping Using a Novel Image-Analysis Pipeline, PANorama, Plant Physiol., 165(2):479-95 (2014).
(Continued)

*Primary Examiner* — Md M Rahman
(74) *Attorney, Agent, or Firm* — Marshall, Gerstein & Borun LLP

(57) ABSTRACT

The invention relates to a method and apparatus for measuring inflorescence, seed and/or seed yield pheno-type of a plant. More particularly, the invention relates to a method and apparatus for high throughput analysis of inflorescence, seed and/or seed yield phenotype of a panicle-like bearing plant.

11 Claims, 4 Drawing Sheets

Related U.S. Application Data

(60) Provisional application No. 62/265,465, filed on Dec. 10, 2015.

(51) Int. Cl.
  *G01N 15/14* (2006.01)
  *G01N 21/85* (2006.01)
  *G01N 21/84* (2006.01)
  *G01N 15/00* (2006.01)

(52) U.S. Cl.
  CPC ..... *G01N 21/85* (2013.01); *G01N 2015/0065* (2013.01); *G01N 2021/845* (2013.01); *G01N 2021/8466* (2013.01)

(58) Field of Classification Search
  USPC ........................................................ 356/302
  See application file for complete search history.

(56) References Cited

U.S. PATENT DOCUMENTS

| | | |
|---|---|---|
| 2005/0254709 A1 | 11/2005 | Geshwind et al. |
| 2009/0293440 A1* | 12/2009 | Moreira ............. A01D 45/22 56/10.1 |
| 2009/0326383 A1 | 12/2009 | Barnes et al. |
| 2010/0142751 A1 | 6/2010 | Hirose |
| 2011/0167721 A1* | 7/2011 | Lejeune ............. B65G 43/00 47/65 |
| 2013/0137961 A1 | 5/2013 | Barnes et al. |
| 2013/0164175 A1* | 6/2013 | Kim ................. G01N 35/1081 422/64 |
| 2014/0154152 A1* | 6/2014 | Chumanov ........ G01J 3/0291 422/561 |

OTHER PUBLICATIONS

European patent application No. 15199373.0, Extended European Search Report, dated May 24, 2016.
Ikeda et al., Analysis of rice panicle traits and detection of QTLs using an image analyzing method, Breeding Sci., 60:55-64 (2010).
International Application No. PCT/EP2016/079952, International Search Report, dated Jan. 30, 2017.

* cited by examiner

METHOD AND APPARATUS FOR MEASURING INFLORESCENCE, SEED AND/OR SEED YIELD PHENOTYPE

CROSS-REFERENCE TO RELATED APPLICATIONS

This is a division of U.S. patent application Ser. No. 16/060,081, filed Jun. 7, 2018 and incorporated herein by reference in its entirety, which is a U.S. national stage entry of International Application No. PCT/EP2016/079952, filed Dec. 6, 2016, which claims the benefit of U.S. Provisional Application No. 62/265,465, filed Dec. 10, 2015 and European Application No. 15199373.0, filed Dec. 10, 2015.

TECHNICAL FIELD

This invention relates to evaluation of inflorescence, seed and/or seed yield phenotype of plants.

More in particular, the invention relates to a method and apparatus for evaluation of inflorescence, seed and/or seed yield phenotype of panicle-like bearing plants.

BACKGROUND ART

In breeding of plants cultivated for their seeds (also called seed crops) for example rice, wheat, barley, corn, soybean, canola, sunflower, millet and safflower, a major goal is to find genotypes that have a high seed yield. Breeders often have to analyse the seed yield of large populations of plants with different genotypes, obtained for example through sexual crossing of parental lines. Molecular breeders, who create variability by insertion of transgenes in a plant species, also have to cope with large plant populations of which the seed yield needs to be assessed. Tools for fast, accurate and efficient measurement of seed yield are a necessity for the plant breeding industry.

Plant phenotyping starts in essence with the creation of genotypic variation among plants of a given species. Following the creation of genotypic variation, selection of those genotypes having the most desirable agronomic phenotypes is performed. For example, plants may be selected for certain reproductive features such as: inflorescence number, size, or architecture, number of seeds per inflorescence, seed size, seed number, and seed weight. Such features contribute to the final seed yield and are called "yield components". Traditional methods for evaluating yield components involve labour-intensive procedures such as manual and visual measurements of dimensions, counting of plant parts, and weighing of plant parts such as individual inflorescences and seeds. Usually, these operations require detaching the plant parts of interest from the subtending plant organs.

It is one practice to evaluate seed produced by plants by a procedure which involves several steps. The seeds are physically separated from the plant, the harvest step, and then cleaned to remove non-seed remnants originating from the maternal plant and dust or other contaminating particles. Mature seeds are discriminated from improperly matured seeds (hereinafter "immature seeds"), e.g. seeds that are not completely filled. In most cases the ratio of mature seeds versus immature seeds is recorded as a parameter that is relevant for the breeders. The mature seeds are weighed and counted, so that the total mature seed weight which is an important parameter for breeders, can be derived as well as the average weight per mature seed which gives a value for comparison with for example, the thousand kernel weight that is commonly used as an important parameter by breeders.

For example in rice plant phenotyping, it is common practice to measure seed yield by harvesting the mature panicles or seed bearing plant inflorescences at the end of the experiment of growing a plant. The panicles/inflorescences are then threshed and all the seeds are collected and counted. The seeds are usually covered by a dry outer covering, the husk. The filled husks (herein also named filled florets) can be separated from the empty ones using an air-blowing device. The empty husks can be discarded and the remaining fraction can be counted again. The filled husks can be weighed on an analytical balance. The total number of seeds is then determined by counting the number of filled husks that remained after the separation step. The total seed weight is measured by weighing all filled husks harvested from a plant. The total number of seeds (or florets) per plant can be determined by counting the number of husks (whether filled or not) harvested from a plant. Thousand Kernel Weight (TKW) can be extrapolated from the number of seeds counted and their total weight. The number of flowers per panicle can be calculated as being the ratio between the total number of seeds over the number of mature primary panicles. And the "seed fill ratio" or "seed filling ratio" can be calculated as being the proportion (expressed as a %) of the number of filled seeds (i.e. florets containing seeds) over the total number of seeds (i.e. total number of florets). In other words, the seed filling ratio is the percentage of florets that are filled with seed.

This manual seed harvesting and subsequent analysis steps are a very time and cost involving process.

Instruments used for conducting these measurements in such a procedure include balances for measuring seed weight and seed counters for counting the number of seeds, all of which exist in different commercially available types. One type of seed counter comprises an inlet for a batch of seed, a system that allows the seeds to drop one by one, and a system to detect each particle of a defined size that passes in front of an optical detector. Instruments for cleaning the seeds also exist in different commercially available types. Some are based on the passage of seeds over sets of shaking sieves with different mesh size, until seeds of the right particle size are retained on one of those sieves. Other instruments are based on the differential aerodynamic and/or gravity properties of seeds versus contaminants in a fluid flow, usually a stream of air. Discrimination of matured versus immature seeds can also be done based on the principle of differential aerodynamic/gravity properties.

EP1431744 describes an improved apparatus for the determining and recording characteristics of seed in a batch of plant product.

Another way of determining characteristics of seed in a batch of plant product can be found in EP1332354 which describes using spectral data signals to determine whether a seed exhibit a specific trait.

Disadvantages related to above referred methods and instruments is that they require a step of physically separating the seeds from the rest of the plant, which is time consuming and thereby also losing information on traits which might enable breeders to gain more insights in flowering and seed forming mechanisms of the crops under evaluation.

In 2009, Gray et al. developed a new method for estimating seed production of plants (Gray et al., 2009 New technology for estimating seed production of moist-soil plants. *Journal of Wildlife Management* 73:1229-1232) and recommended to use desktop scanners to predict seed yield of a press-dried panicle. This method does not permit to work in a high throughput manner as it needs manual handling before the analysis can start.

DISCLOSURE OF INVENTION

It is therefore an object of the present invention to provide a device and methods which at least partially avoid the disadvantages and shortcomings of the systems and methods known from the prior art.

The present invention overcomes these shortcomings by providing an apparatus and method for non-destructive analysis of the physical characteristics of the inflorescence, seeds and/or seed yield of panicle-like bearing plants. In a preferred embodiment also the chemical characteristics of the inflorescence, seed and/or seed yield of the plants are analysed. As such, analysis results include, but are not limited to, seed yield; seed or grain quantity; seed or grain quality; oil yield; content of oil, starch and/or protein in harvested organs (e.g., seeds); number of flowers (florets) per panicle or alternatively the number of flowers can also be expressed as a ratio of number of filled seeds over number of primary panicles; harvest index; number and size of harvested organs per plant and per area; number of harvested organs in field; number of harvestable organs (e.g. seeds), seeds per pod, weight per seed; and modified architecture (such as increased stalk diameter, thickness, branching, or improvement of physical properties).

The invention further relates to a method and apparatus for screening at least one panicle-like bearing plant specimen to evaluate its inflorescence, seed and/or seed yield phenotype in seed-bearing plants. The invention further relates to a tracking method for tracking growth conditions of a plurality of plant specimens, a method for phenotyping, for selecting the most desired genotypes based on phenotype scoring, and to a method for rapid analysis of stress resistance of growing plant specimens. Biotic stress can be caused, for example, by bacterial, fungal, or viral disease, insects and nematodes. Abiotic stress can be caused, for example, by heat, drought, cold, wind, high salinity, and low or too high nutrient levels.

Devices and methods of this kind may be applied in all fields of agricultural research and commercial activities and in all fields of chemical and/or biological technology related to plants and plant specimens. Preferably, the device and methods according to the present invention may be applied to the technical field of testing of plants and testing of methods for treatment of plants, such as one or more of: testing and/or evaluation of optimum growth conditions; testing of resistance of plants against specific types of stress; testing of specific fertilizers and/or nutrients; the selection and/or breeding of plants having one or more desired properties; the testing of the effect and/or effectiveness of specific treatments, such as 20 treatments of the plants or plant specimens with fertilizers and/or pesticides. However, other applications of the present invention are possible.

It is therefore a further objective of the present invention to provide a device and methods for screening plants, especially plants bearing a panicle, more specifically grass-like plants.

Here, we describe a method and apparatus for non-destructive analysis of the inflorescence, seed and/or seed yield phenotype of a panicle, which reduces dramatically the amount of labour compared to traditional methods because most manual handling steps are replaced by automated imaging procedures. The method and apparatus described herein enable a high throughput analysis of panicles as these enable continuous processing of the provided panicles. Preferably, the methods and apparatus of the present invention provide a fully automated image processing.

Further advantages of the invention will become apparent from the following description.

In a preferred aspect the above method and apparatus is using hyper-spectral imaging in the near infrared range which enables to predict basic chemical components of the plants' inflorescence or seeds, such as content of starch, protein, moisture, and oil.

Plants that can be evaluated by the present method and apparatus can be any plant having a panicle-like inflorescence. These plants may be different varieties, hybrids, inbreds or a population of e.g. grass like plants, such as rice, oats, wheat, barley, rye, sorghum, sudangrass, Kentucky bluegrass, tall fescue, but also corn, canola, . . . inflorescences or panicle could be evaluated using the method and apparatus of this invention.

For the purposes of this description the wording "panicle" is defined as an elongated inflorescence with a central axis along which are branches that are themselves branched, including elongated racemes and/or groups of racemes, with long pedicels/peduncles providing a more or less loose aspect and spikes with a bilateral symmetry. Examples of plants having such panicle are rice, oats, sudangrass, Kentucky bluegrass, and sorghum.

As used herein the phrase "seed yield" can be, but not limited to, the number or weight of the seeds per plant, seeds per pod, or to the weight of a single seed, or to the oil, protein and/or starch content per seed or to the oil, protein and/or starch content per plant or per panicle. Hence seed yield can be affected by, but not limited to, seed dimensions (e.g., length, width, perimeter, area and/or volume), number of (filled) seeds and seed filling rate and by seed oil content. Hence increased seed yield per plant could affect the economic benefit one can obtain from the plant in a certain growing area and/or growing time.

The term "seed" (also referred to as "grain" or "kernel") as used herein refers to a small embryonic plant enclosed in a covering called the seed coat (usually with some stored nutrients), the product of the ripened ovule of gymnosperm and angiosperm plants which occurs after fertilization and some growth within the mother plant. For the purposes of this description, the term seed also encompasses 'fruit', which, according to the Merriam-Webster, is the part of the plant that has the seeds in it (such as the pod of a pea, a nut, a grain or a berry).

The phrase "oil content" as used herein refers to the amount of lipids in a given plant organ, either the seeds (seed oil content) or the vegetative portion of the plant (vegetative oil content) and is typically expressed as percentage of dry weight (10 percent humidity of seeds) or wet weight (for vegetative portion).

It should be noted that oil content is affected by intrinsic oil production of a tissue (e.g., seed, vegetative portion), as well as the mass or size of the oil-producing tissue per plant or per growth period.

The phrase "protein content" as used herein refers to the amount of protein in a given plant organ, either the seeds (seed protein content) or the vegetative portion of the plant (vegetative protein content) and is typically expressed as percentage of dry weight or wet weight.

The phrase "starch content" as used herein refers to the amount of starch in a given plant organ, either the seeds (seed starch content) or the vegetative portion of the plant (vegetative starch content) and is typically expressed as percentage of dry weight or wet weight.

An aspect of the present invention provides a method for measuring inflorescence, seed and/or seed yield phenotype of a panicle. The method comprises following steps: a first and second conveyor belt system are provided and also an imaging system is provided. The first and second conveyor belt systems run simultaneously and in opposite directions, resulting in a movement of the transported material in one direction. The second conveyor belt system is placed face-to-face with the first conveyor belt system such that said first and second conveyor belt systems perform a squeezing or gripping action. A panicle, which is cut from a plant, is provided to the first and second conveyor belt system. Preferably the panicle is provided to the conveyor belt systems with the tip of the panicle first in the running direction of both conveyor belt systems.

These first and second conveyor belt systems are made to take the panicle downward. Preferably the panicle is taken to a position wherein the panicle axis is parallel to the gravity direction. In a preferred embodiment, the first and second conveyor belt systems end substantially simultaneously. In another preferred embodiment, one of the conveyor belt systems further assists the transportation of the panicle towards and/or in front of the imaging system.

At the end of the gripping conveyor systems the panicle is presented to the imaging system. As such, the panicle is hanging freely due to gravity forces. In the preferred embodiment wherein the panicle is taken to a position wherein the panicle axis is parallel to the gravity direction, the panicle is hanging completely straight due to gravity forces. The imaging system, which is preferably positioned such that it is imaging in a direction perpendicular to the movement direction of the panicle, acquires at least one spatially resolved image. Preferably, thereafter, the panicle is released from these gripping first and second conveyor belt systems into a collector bin. The phenotype is measured from the image by appropriate software.

An example of such software is described by Crowell et al. in Plant Physiol. 2014 Apr. 2; 165 (2): 479-495.

The software may be driven by an image analysis device. The image analysis device may be adapted to perform at least one image analysis of at least one of the images, preferably the image analysis device may be adapted to generate at least one phenotype or trait of the inflorescence, seed and/or seed yield of a panicle. The term generate according to the present invention may refer to deriving e.g. from the image analysis.

If desired, algorithms may be used to evaluate the measured phenotype. This can also be done by the image analysis device.

The term image, as used in the present invention, may imply any type of images, preferably at least two-dimensional images. The images may be optical images. The images may be built from energetic value readings from any electromagnetic radiation propagated from the imaged object, as such the images may comprise transmission images and/or shadow images and/or reflection images. The images may be generated by detecting an emission signal, e.g. a fluorescence and/or phosphorescence signal. Thus, the images may be generated by chlorophyll fluorescence measurements and/or selectable marker fluorescence measurements. The signal which may be used to generate an image may be discrete in time or may be a continuous signal. Other types of images are also possible as e.g. described hereunder.

From the above it follows that the term imaging, as used in the present invention, may imply any way of acquiring images.

Preferably, the first conveyor belt system has a free running zone. In that case, the second conveyor belt system is placed downstream of the free running zone of the first conveyor belt system. A panicle is then placed on the free running zone of this first conveyor belt system, preferably with the tip of the panicle first in the running direction of the first conveyor belt system. The panicle is then moved forward on said first conveyor belt system towards the second conveyor belt system and the panicle is then squeezed or gripped between both first and second conveyor belt systems downstream of said free running zone.

In a preferred embodiment, said first conveyor belt system consists of one belt. In an alternative embodiment, said first conveyor belt system comprises at least one belt, preferably two or more consecutive conveyor belts. In another preferred embodiment, said second conveyor belt system consists of one belt. In an alternative embodiment, said second conveyor belt system comprises at least one belt, preferably two or more consecutive conveyor belts. In another embodiment, said first and second conveyor belt systems each consist of one belt.

The imaging system comprises at least one detector.

The term detector, as used in the present invention, may imply any type of detector, preferably a detector for electromagnetic radiation (EM-radiation). The term electromagnetic radiation, as used in the present invention, may comprise light in the visible range, X-ray, UV, infrared and near-infrared, thermal and terahertz radiation. It may be broad spectrum or narrow spectrum. It may comprise monochromatic EM-radiation as well as a broad spectrum EM-radiation and it may comprise incoherent EM-radiation as well as coherent EM-radiation, polarised and unpolarised EM-radiation. Other types of electromagnetic waves/radiation are also possible. More preferably the detector may comprise a detector for light in at least one spectral wave length region selected from a visible, an infrared and ultraviolet wavelength region and most preferably a camera. The camera may be a digital camera, preferably with spatial and/or time resolution. More preferably, the camera is a line scan camera.

In a preferred embodiment, the imaging system is imaging in a dust free environment.

In another preferred embodiment, the imaging system is imaging in open air.

Preferably, the methods described herein are used for measuring seed yield when the evaluated panicle bears seeds, preferably at the final maturity stage.

Preferably, each plant panicle is linked to an identifier. Preferably, the identifier may be or may comprise, but is not limited to, one or more of the following identifiers: a barcode; a contactless electronic identifier, i.e. an identifier comprising at least one piece of information, which may be read from the identifier, preferably without any physical contact between a reading mechanism, preferably a reader, and the identifier, most preferably the identifier may be at least one radio frequency identification tag (RFID tag). However, alternatively or additionally, other types of identifiers are possible. The information may be a simple identification, e.g. a plant specimen and/or a genotype and/or growth conditions and/or treatment. In general, the at least one identifier not necessarily has to be in physical contact with the panicle, but should be assigned to a respective panicle in any unambiguous way. The information resulting from the measurement of the phenotype from the image by appropriate software is preferably also associated to the identifier.

In an even more preferred embodiment, the method also comprises a step of directing electromagnetic radiation to the panicle, such that the panicle propagates electromagnetic radiation. The panicle is then imaged at different wavelengths wherein images comprising pixels are obtained. These images recorded at different wavelengths are aligned on the basis of the pixels, such that a 3-dimensional image is generated. The 3-dimensional image, the imaging cube, comprises 2 spatial dimensions and 1 spectral dimension. In the next step of this method, a customary predictive mathematical model combining the weighted contributions of the different wavelengths is used to correlate the multispectral or hyperspectral imaging cube of the panicle to a phenotype and the phenotype is then measured from said correlation by appropriate software.

The electromagnetic radiation propagated from the panicle is preferably transmitted light. In another preferred embodiment, the electromagnetic radiation propagated from the panicle is reflected light.

In a preferred embodiment the images are collected at many different narrow wavebands in the near infrared range of the light spectrum, preferably between 900 and 1700 nanometers.

The methods of the present invention can be used to detect any phenotype that can be measured by imaging. In one preferred embodiment, the phenotype is one or more of a quantitative trait, a biochemical trait and a morphological trait. In an even more preferred embodiment, the biochemical trait is selected from the group consisting of oil composition, protein composition, carbohydrate composition, fiber composition, oil content, protein content, carbohydrate content, starch content, fiber content, dry weight and water content. In another even more preferred embodiment, the morphological trait is selected from inflorescence architecture, flower size, flower shape, flower color, flower surface texture, flower weight, flower integrity, endosperm size, germ size, seed shape, seed size, seed color, seed surface texture, seed weight, seed density, and seed integrity. As used herein, integrity is correlated to susceptibility or resistance to any one of diseases, insect infestation, and fungal infestation. In an alternative preferred embodiment, the quantitative trait is selected from amount of florets, amount of seeds, amount of empty seeds, amount of branching, weight of seeds, total weight of seeds and/or fill rate. However, other types of parameters and/or combinations of the named parameters and/or other parameters may be possible, e.g. number and size of harvested organs per plant; content of oil, starch and/or protein in harvested organs (e.g., seeds or vegetative parts of the plant); number of flowers (florets) per panicle or alternatively the number of flowers can also be expressed as a ratio of number of filled seeds over number of primary panicles for one plant; or modified architecture (such as increased stalk diameter, thickness, branching or improvement of physical properties).

The methods of the present invention can be used to analyse the impact of genetic modifications on plants, and in particular on inflorescence, seed and/or seed yield phenotype of its panicles, and selecting a panicle and/or seeds with a genetic modification of interest. Such method comprises following steps: first a plurality of plants with differing genotypes are grown till they have panicles. Preferably, populations or groups of plants with the same genotype are grown together with populations or groups of plants with differing genotypes, all are grown till they have panicles. Preferably each plant is associated with an identifier, more preferably a machine readable identifier that distinguishes the plant from other plants. In case a population or group of plants with the same genotype is used, each plant is assigned to a same genotype identifier. Images are then obtained using the methods described herein and these images are then analysed for one or more phenotypes and/or traits as described above, to determine the impact of the genetic modification. A selection can then be made for a population, plant, panicle or seed(s) with a genetic modification of interest. If desired, algorithms may be used to select and evaluate the measured phenotype(s) and the results statistically analyzed to identify plants with genetic modifications of interest, for selecting the best performing candidates or discarding the poorest performing plants/population(s) or for selecting candidates having any given characteristics for any given further process, and/or identifying trait leads.

The creation of genotypic variation can be based on genetic modifications made in the laboratory, but can also rely on the production of genetic alterations that can be obtained by techniques including recombination through crossing, chemical mutagenesis, radiation-induced mutation, somatic hybridisation, inter-specific crossing and genetic engineering. The obtained plants can be compared to other non-transgenic plants, to other transgenic plants and/or to corresponding control plants. Following the creation of genotypic variation, selection of those genotypes having the most desirable agronomic phenotypes is performed.

The invention provides in another of its aspects a process for evaluating and recording characteristics of panicles, such as seed and/or seed yield of a plant comprising the steps of identifying the plant, providing the panicles to the apparatus as described above, determining the average weight of the seeds in the first fraction, processing the results to determine the ratio of mature seeds in the batch to improperly matured seeds and recording results in a prescribed format in a computer database together with the plant identifier.

Another aspect of the invention provides an improved imaging system which significantly increases the throughput of seed imaging with a very high accuracy.

Another aspect of the invention relates to an improved method for processing and/or analysing seed in preparation for growing or for selection of plants with a genetic modification of interest.

The computer database compiled by subjecting plant panicles to a process as aforesaid may be interrogated and enables rapid comparison of characteristics from a multitude of different plants and thus permits rapid determination of seeds from which further plants may be derived which yield seeds having desired characteristics.

The invention provides in another of its aspects a process for comparing one or more of the characteristics of seed yield, average seed weight and/or ratio of mature versus improperly matured seeds in a batch of plant product with corresponding characteristics of other batches of plant product, in which a computer database compiled by subjecting batches of plant product to a process according to the last preceding paragraph but one is interrogated concerning said one or more characteristics.

Another aspect of the invention provides an apparatus for high-throughput evaluation of inflorescence, seed and/or seed yield of a panicle, wherein the apparatus comprises an imaging system and a transporter for supporting and moving said plant panicle to said imaging system, and wherein the transporter comprises two conveyor belt systems. These two conveyor belt systems are placed face-to-face for gripping a panicle to be evaluated. Preferably the transporter provides spreading of the flowers and/or seeds on the panicle such that said flowers and/or seeds, when exiting the transporter, are all in one plane to be imaged by the imaging system. Preferably, the flowers and/or seeds are in one plane perpendicular to the imaging system.

Preferably, the apparatus also comprises a system providing position registration of the panicle.

These first and second conveyor belt systems are made to take the panicle downward. Preferably, the panicle is taken to a position wherein the panicle axis is parallel to the gravity direction. In a preferred embodiment, the first and second conveyor belt systems end substantially simultaneously. In another preferred embodiment, one of the conveyor belt systems further assists the transportation of the panicle towards and/or in front of the imaging system.

At the end of the gripping conveyor systems the panicle is presented to the imaging system. As such, the panicle is hanging downward due to gravity forces. In the preferred embodiment, wherein the panicle is taken downward to a position wherein the panicle axis is parallel to the gravity direction, the panicle will be hanging completely straight due to gravity forces. The imaging system, which is preferably positioned such that it is imaging in a direction perpendicular to the movement direction of the panicle, acquires at least one image. Thereafter, the panicle is released from these gripping first and second conveyor belt systems into a collector bin. The phenotype is measured from the image by appropriate software.

An example of such software is described by Crowell et al. in Plant Physiol. 2014 Apr. 2; 165 (2): 479-495.

If desired, algorithms may be used to evaluate the measured phenotype.

The imaging system comprises at least one detector.

The term detector, as used in the present invention, may imply any type of detector, preferably a detector for electromagnetic radiation. The term electromagnetic radiation, or EM-radiation, as used in the present invention, may comprise light in the visible range, infrared and near-infrared, thermal and terahertz radiation. It may be broad spectrum or narrow spectrum. It may comprise monochromatic EM-radiation as well as a broad spectrum EM-radiation and it may comprise incoherent EM-radiation as well as coherent EM-radiation, polarised and/or unpolarised EM-radiation. Other types of electromagnetic waves/radiation are also possible. More preferably the imaging system may comprise a detector for light in at least one spectral wave length region selected from a visible, an infrared and ultraviolet wavelength region and most preferably a camera. The camera may be a digital camera, preferably with spatial and/or time resolution. More preferably, the camera is a line scan camera.

The apparatus may further comprise at least one image analysis device. The image analysis device may be adapted to perform at least one image analysis of at least one of the images, preferably the image analysis device may be adapted to generate at least one phenotype or trait of the inflorescence, seed and/or seed yield of a panicle. The term generate according to the present invention may refer to deriving e.g. from the image analysis. The image analysis device may use appropriate software as described above, and can also use algorithms to evaluate the measured phenotype.

The apparatus may further also comprise an identifier reader to identify an identifier linked to said panicle, the reader preferably providing output in digital form. Examples of such a reader are, but are not limited to, a barcode reader, a transponder reader and an RFID reader. In a preferred embodiment, the apparatus further comprises at least one electronic code reading device to identify an identifier linked to said panicle. The identifier reader is preferably integrated by use of software in a computer device and fed therefrom to the database.

The apparatus further may have at least one database for recording data regarding the inflorescence, seed and/or seed yield of a panicle. The data preferably may be at least one of the following: at least one image of the plant panicle; at least one phenotype or trait derived from at least one image of the plant panicle; information from the identifier. As outlined above, the at least one phenotype or trait may comprise one or more parameters characterizing the phenotype of the plants' panicle or seed or seed yield. The at least one phenotype or trait may preferably be chosen from: one or more of a quantitative trait, a biochemical trait and a morphological trait. In a preferred embodiment, the biochemical trait is selected from the group consisting of oil composition, protein composition, carbohydrate composition, fiber composition, oil content, oil yield, protein content, carbohydrate content, starch content, fiber content, dry weight and water content. In another preferred embodiment, the morphological trait is selected from inflorescence architecture, flower size, flower shape, flower color, flower surface texture, flower weight, flower integrity, endosperm size, germ size, seed shape, seed size, seed color, seed surface texture, seed density, seed yield; seed or grain quantity, and seed integrity. As used herein, integrity is correlated to susceptibility or resistance to any one of diseases, insect infestation, and fungal infestation. In an alternative preferred embodiment, the quantitative trait is selected from amount of florets, amount of seeds, amount of empty seeds, amount of branching, weight of seeds, total weight of seeds and/or fill rate.

However, other types of parameters and/or combinations of the named parameters and/or other parameters may be possible, e.g. number and size of harvested organs per plant and per area; content of oil, starch and/or protein in harvested organs (e.g., seeds or vegetative parts of the plant); number of flowers (florets) per panicle or alternatively the number of flowers can also be expressed as a ratio of number of filled seeds over number of primary panicles for one plant; or modified architecture (such as increased stalk diameter, thickness, branching or improvement of physical properties).

The database may be manipulated to inspect and compare data to determine various characteristics such as the amount of seeds and the ratio filled-non-filled seeds or the average weight of seeds.

Apparatus according to the invention permits derivation of data about inflorescence and/or seed without human intervention other than perhaps initial feeding of the panicles to the inlet and/or removal of panicles from the apparatus. It may be used for a variety of purposes and is especially useful for evaluation of mature seeds on a panicle obtained by harvesting one or more plants. In such use, the apparatus provides an integrated automatic process for evaluating seed and/or seed yield of a harvested plant or plants. By use of the apparatus one may derive in a single operation desired data about key parameters of interest to the plant breeder such as amount of seeds per panicle and/or per plant, seed size, seed yield, average seed weight and ratio of matured to immature seed in the batch.

The apparatus furthermore may comprise a control system which may be adapted to control and/or to drive the imaging system and/or transporter and/or the conveyor belt systems and/or the image analysis device and/or the reader and/or the database and/or a power supply. The control system may comprise a computer and electrical and/or signal connectors, preferably electrical lines and interfaces.

Preferably, the imaging system is shielded from natural daylight. Light inside the imaging system may be provided by a set of lamps of which the intensity can be controlled.

Images taken in the imaging system can be processed on-line using imaging analysis software to extract information on the panicles and preferably downloaded to a computer. Prefereably, the processed data as well as the images get linked to a unique identifier and even more preferably, downloaded to a computer.

Preferably, the first conveyor belt system has a free running zone. In that case, the second conveyor belt system is placed downstream of the free running zone of the first conveyor belt system. A panicle is then placed on the free running zone of this first conveyor belt system, preferably with the tip of the panicle first in the running direction of the first conveyor belt system. The panicle is then moved forward on said first conveyor belt system towards the second conveyor belt system and the panicle is then squeezed or gripped between both first and second conveyor belt systems downstream of said free running zone.

In a preferred embodiment, said first conveyor belt system consists of one belt. In an alternative embodiment, said first conveyor belt system comprises at least one belt, preferably two or more consecutive conveyor belts. In another preferred embodiment, said second conveyor belt system consists of one belt. In an alternative embodiment, said second conveyor belt system comprises at least one belt, preferably two or more consecutive conveyor belts. In another embodiment, said first and second conveyor belt systems each consist of one belt.

In a preferred embodiment, the imaging system comprises the following:
- at least one digital camera with sensitivity in the near-infrared range;
- at least one light source with suitable spectral composition in the near infrared range to illuminate said panicle,
- at least one spectrograph composed of an optical dispersing element such as a grating or prism to split the incoming light into many narrow, adjacent wavelength bands, said spectrograph being placed before the camera;
- at least one suitable optical lens;
- computer hardware elements and connections to the different previous elements and
- dedicated software elements for driving signal outputs and inputs from and to the hardware elements, and automatically perform the different steps of the method described herein.

Such imaging is often referred to in literature as imaging spectroscopy, which is the simultaneous acquisition of spatially co-registered images in many spectrally contiguous bands. The image produced by such imaging spectroscopy is similar to an image produced by a digital camera, except each pixel has many bands of light intensity data instead of just three bands: red, green, and blue. In the art, the wording "hyper spectral" data sets are described as being composed of relatively large number (e.g., 100-1000) spectral bands of relatively narrow bandwidths (e.g., 1-10 nm), whereas, "multi-spectral" data sets are usually fewer (e.g., 5-10) bands of relatively large bandwidths (e.g., 70-400 nm), or fewer bands of relatively narrow bandwidths.

In a preferred embodiment, the imaging system comprises a hyperspectral camera. In another preferred embodiment, the imaging system comprises a multispectral camera.

Preferably, the imaging system described above comprises a spectrograph being tunable so that specific wavebands can be selected and transmitted to the camera in a predetermined sequence.

Another aspect of the present invention provides for the use of an apparatus as described herein for measuring inflorescence, seed and/or seed yield phenotype. Preferably, such an apparatus is used in the methods as described herein.

In another aspect, the apparatus as described herein can be used in a method for comparing the effects of different growth conditions of plants.

In an alternative aspect, the apparatus as described herein can be used in a method for phenotyping, for selecting the most desired genotypes based on phenotype scoring.

In another alternative aspect, the apparatus as described herein can be used in a method for analysis of stress resistance of plant specimens.

In another alternative aspect, the apparatus as described herein can be used in a method for determining maturity of seeds on a panicle.

In a further alternative aspect, the apparatus as described herein can be used in a method for testing of methods for treatment of plants, such as one or more of: testing and/or evaluation of optimum growth conditions; testing of resistance of plants against specific types of stress; testing of specific fertilizers and/or nutrients; the selection and/or breeding of plants having one or more desired properties; the testing of the effect and/or effectiveness of specific treatments, such as 20 treatments of the plants or plant specimens with fertilizers and/or pesticides.

Summarizing the ideas of the present invention, the following embodiments are preferred:

EMBODIMENT 1

Method for measuring inflorescence, seed and/or seed yield phenotype of a panicle, comprising:
- providing a first and second conveyor belt system and an imaging system;
- said conveyor belt systems are placed face-to-face, and run simultaneously and in opposite directions, resulting in a movement of the transported material in one direction, such that said first and second conveyor belt systems perform a gripping action;
- providing panicle cut from a plant;
- providing said panicle to the first and second conveyor belt systems;
- said first and second conveyor belt systems taking the panicle downward;
- presenting said panicle at the end of the gripping conveyor systems to said imaging system;
- said imaging system acquiring at least one spatially resolved image, and
- measuring the phenotype from said image by appropriate software.

EMBODIMENT 2

Method according to embodiment 1, wherein said first conveyor belt system comprises a free running zone and wherein said second conveyor belt system is placed downstream of the free running zone of the first conveyor belt system; said method further comprising:
- placing said panicle on the free running zone of said first conveyor belt system;
- moving said panicle forward on said first conveyor belt system towards said second conveyor belt system;

gripping said panicle between both first and second conveyor belt systems downstream of said free running zone.

EMBODIMENT 3

Method according to any one of embodiment 1 or 2, wherein each of said conveyor belt systems comprises at least one belt, preferably consists of one conveyor belt.

EMBODIMENT 4

Method according to any one of the previous embodiments, wherein said imaging system comprises at least one detector, preferably at least one camera, more preferably at least one digital camera, most preferably at least one line scan digital camera.

EMBODIMENT 5

Method according to any one of the previous embodiments, wherein said imaging system is imaging in a dust free environment.

EMBODIMENT 6

Method according to any one of the previous embodiments, wherein said imaging system is imaging in open air.

EMBODIMENT 7

Method according to any one of the previous embodiments, for measuring seed yield wherein said panicle bears seeds.

EMBODIMENT 8

Method according to any one of the previous embodiments, wherein said plant panicle is linked to an identifier.

EMBODIMENT 9

The method according to any of the previous embodiments, wherein said plant panicle bears seeds at the final maturity stage.

EMBODIMENT 10

Method according to any one of the previous embodiments, said method further comprising:
- directing electromagnetic radiation onto said panicle, said panicle thereby propagating electromagnetic radiation;
- imaging said panicle at different wavelengths thereby obtaining images comprising pixels;
- aligning said images recorded at different wavelengths on the basis of said pixels, thereby generating a 3-dimensional imaging cube, said 3-dimensional imaging cube comprising 2 spatial dimensions and 1 spectral dimension;
- using a customary predictive mathematical model combining the weighted contributions of the different wavelengths, thereby correlating the multispectral or hyperspectral imaging cube of said panicle to a phenotype;
- measuring the phenotype from said imaging cube by appropriate software.

EMBODIMENT 11

Method according to embodiment 10 for measuring seed yield, wherein said panicle bears seeds.

EMBODIMENT 12

Method according to any one of the previous embodiments 10 or 11, wherein said plant panicle is tagged.

EMBODIMENT 13

The method according to any of the previous embodiments 10 to 12, wherein said plant panicle bears seeds at the final maturity stage.

EMBODIMENT 14

The method according to any of the previous embodiments 10 to 13, wherein said images are collected at many different narrow wavebands in the near infrared range of the light spectrum, preferably between 900 and 1700 nanometers.

EMBODIMENT 15

The method according to any of the previous embodiments, wherein said phenotype is one or more of a quantitative trait, a biochemical trait and a morphological trait.

EMBODIMENT 16

The method according to embodiment 15, wherein said biochemical trait is selected from the group consisting of oil composition, protein composition, carbohydrate composition, fiber composition, oil content, protein content, carbohydrate content, starch content, fiber content, dry weight and water content.

EMBODIMENT 17

The method according to embodiment 15, wherein said morphological trait is selected from inflorescence architecture, endosperm size, germ size, seed shape, seed size, seed color, seed surface texture, seed weight, seed density, and seed integrity.

EMBODIMENT 18

The method according to embodiment 17, wherein said seed integrity is correlated to susceptibility or resistance to any one of diseases, insect infestation, and fungal infestation.

EMBODIMENT 19

The method according to embodiment 15, wherein said quantitative trait is selected from amount of florets, amount of seeds, amount of empty seeds, amount of branching, weight of seeds, total weight of seeds, fill rate.

EMBODIMENT 20

Apparatus for high-throughput evaluation of inflorescence, seed and/or seed yield of a panicle, which comprises:

an imaging system;
a transporter for supporting and moving said panicle to said imaging system,
said transporter comprising two conveyor belt systems, said systems being placed face-to-face for gripping a panicle to be evaluated.

EMBODIMENT 21

Apparatus according to embodiment 20, wherein said transporter for supporting and moving said panicle provides spreading of the seeds such that said seeds are all visible in one plane by the imaging system.

EMBODIMENT 22

Apparatus according to embodiment 20 or 21, wherein said each conveyor belt system comprises at least one conveyor belt.

EMBODIMENT 23

Apparatus according to any one of the embodiments 20 to 22, wherein said imaging system comprises at least one detector, preferably at least one digital camera, more preferably at least one line scan digital camera.

EMBODIMENT 24

Apparatus according to any one of the embodiments 20 to 23, wherein said imaging system comprises:
- at least one electromagnetic radiation source with suitable spectral composition in the near infrared range to direct electromagnetic radiation onto said panicle;
- at least one digital camera with sensitivity in the near-infrared range; at least one spectrograph composed of an optical dispersing element such as a grating or prism to split the incoming electromagnetic radiation into many narrow, adjacent wavelength bands, said spectrograph being placed before the camera;
- at least one suitable optical lens;
- computer hardware elements and connections to the different previous elements;
- dedicated software elements for driving signal outputs and inputs from and to the hardware elements, and automatically perform the different steps of the method described in any one of embodiments 1 to 18.

EMBODIMENT 25

Apparatus according to any of the embodiments 20 to 24, said apparatus further comprising at least one electronic code reading device to identify an identifier linked to said panicle.

EMBODIMENT 26

Use of an apparatus according to any one of embodiments 20 to 25 for measuring inflorescence, seed and/or seed yield phenotype.

EMBODIMENT 27

Use of an apparatus according to embodiment 26 in the method of any of the embodiments 1 to 18.

EMBODIMENT 28

Use of an apparatus according to any one of embodiments 26 to 27 in a method for comparing the effects of different growth conditions of plants.

EMBODIMENT 29

Use of an apparatus according to any one of embodiments 26 to 28 in a method for phenotyping, for selecting the most desired genotypes based on phenotype scoring.

EMBODIMENT 30

Use of an apparatus according to any one of embodiments 26 to 29 in a method for analysis of stress resistance of plant specimens.

EMBODIMENT 31

Use of an apparatus according to any one of embodiments 26 to 30 in a method for testing of methods for treatment of plants, such as one or more of: testing and/or evaluation of optimum growth conditions; testing of resistance of plants against specific types of stress; testing of specific fertilizers and/or nutrients; the selection and/or breeding of plants having one or more desired properties; the testing of the effect and/or effectiveness of specific treatments, such as 20 treatments of the plants or plant specimens with fertilizers and/or pesticides.

In order that the invention may become more clear there now follows a description to be read with the accompanying schematic drawings of two example apparatuses according to the invention and their use in a process according to the invention selected for description to illustrate the invention by way of example.

- 110: apparatus for high throughput evaluation
- 120: imaging system
- 121: detector
- 122: spectrograph
- 130: transporter
- 131: first conveyor belt system
- 132: second conveyor belt system
- 140: light/electromagnetic radiation
- 150: image
- 160: image analysis device
- 170: identifier reader
- 190: control system

EXAMPLES

Figure 1:
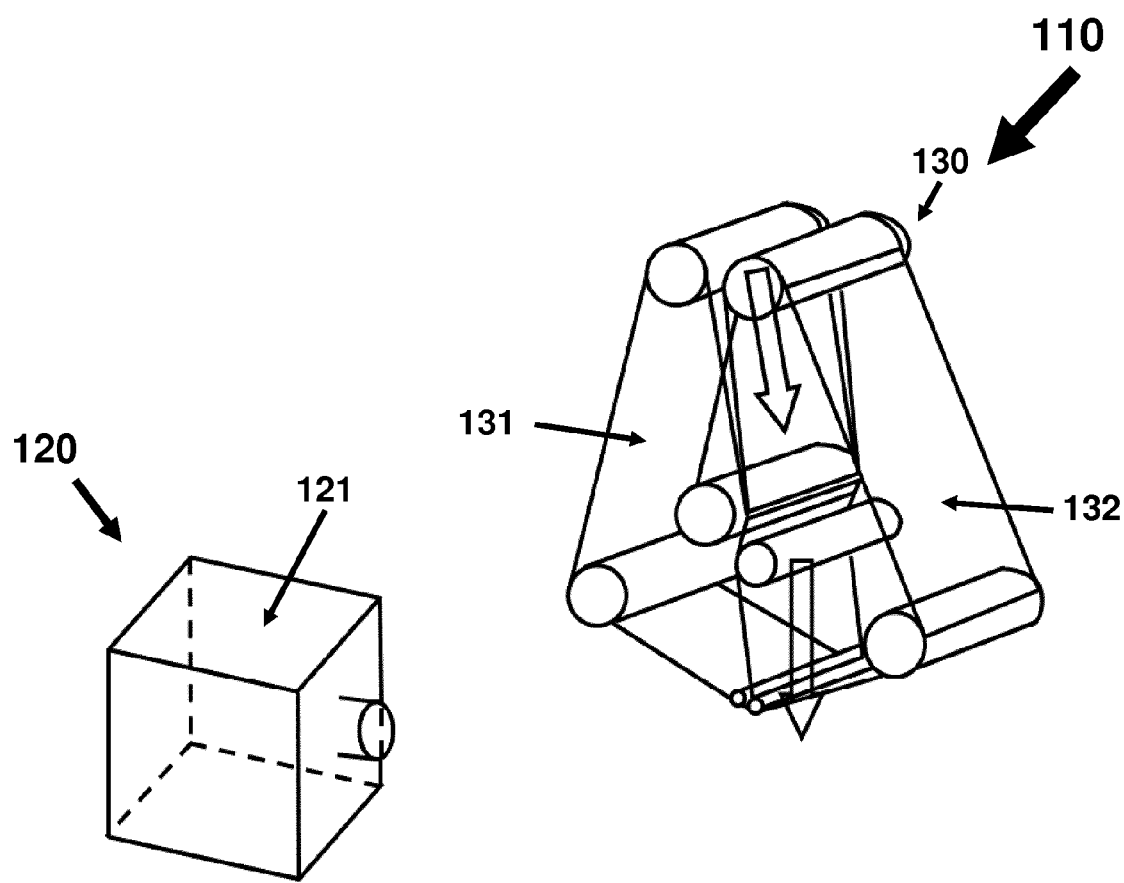
FIG. 1 is a schematic perspective view of one embodiment of an apparatus for high throughput imaging of cut panicles (arrows show the movement of the panicles to the imaging system).

In FIG. 1 an example is shown of an apparatus 110 for high-throughput evaluation of inflorescence, seed and/or seed yield of a panicle, wherein the apparatus comprises an imaging system 120 and a transporter 130 for supporting and moving said plant panicle to said imaging system 120, and wherein the transporter 130 comprises two conveyor belt systems 131, 132. These two conveyor belt systems 131, 132 are placed face-to-face for gripping a panicle to be evaluated. The transporter 130 may provide spreading of the flowers and/or seeds on the panicle such that said flowers and/or seeds, when exiting the transporter 130, are all in one plane to be imaged by the imaging system 120. Preferably, the flowers and/or seeds are in one plane perpendicular to the imaging system 120.

These first and second conveyor belt systems 131, 132 take the panicle downward (shown by the arrows). The panicle may be taken downward to a position wherein the panicle axis is parallel to the gravity direction. In this example, the first and second conveyor belt systems 131, 132 end substantially simultaneously.

At the end of the gripping conveyor systems 131, 132 the panicle is presented to the imaging system 120. As such, the panicle is hanging downward due to gravity forces. When the panicle is taken downward parallel to the direction of gravity, the panicle will be hanging completely straight due to gravity forces. The imaging system 120, which is preferably positioned such that it is imaging in a direction perpendicular to the moving direction of the panicle, acquires at least one image. Thereafter, the panicle is released from these gripping first and second conveyor belt systems 131, 132 into a collector bin (not shown). The phenotype is measured from the image by appropriate software.

An example of such software is described by Crowell et al. in Plant Physiol. 2014 Apr. 2; 165 (2): 479-495.

If desired, algorithms may be used to evaluate the measured phenotype.

The imaging system 120 comprises a detector 121. In this example the detector 121 is a digital camera.

The apparatus may further comprise at least one image analysis device 160 (not shown). The image analysis device 160 may be adapted to perform at least one image analysis of at least one of the images 150, preferably the image analysis device 160 may be adapted to generate at least one phenotype or trait of the inflorescence, seed and/or seed yield of a panicle. The term generate according to the present invention may refer to deriving e.g. from the image analysis.

The apparatus may further also comprise an identifier reader 170 (not shown) to identify an identifier linked to a panicle or a group of panicles. Such a reader can be a barcode reader, a transponder reader and/or an RFID reader. In a preferred embodiment, the apparatus further comprises at least one electronic code reading device to identify an identifier linked to said panicle.

The apparatus further may have at least one database (not shown) for recording data regarding the inflorescence, seed and/or seed yield of a panicle. The data preferably may be at least one of the following: at least one image of the plant panicle; at least one phenotype or trait derived from at least one image of the plant panicle; information from the identifier. As outlined above, the at least one phenotype or trait may comprise one or more parameters characterizing the phenotype of the plants' panicle or seed or seed yield. The at least one phenotype or trait may preferably be chosen from: one or more of a quantitative trait, a biochemical trait and a morphological trait. In a preferred embodiment, the biochemical trait is selected from the group consisting of oil composition, protein composition, carbohydrate composition, fiber composition, oil content, oil yield, protein content, carbohydrate content, starch content, fiber content, dry weight and water content. In another preferred embodiment, the morphological trait is selected from inflorescence architecture, flower size, flower shape, flower color, flower surface texture, flower weight, flower integrity, endosperm size, germ size, seed shape, seed size, seed color, seed surface texture, seed density, seed yield; seed or grain quantity, and seed integrity. As used herein, integrity is correlated to susceptibility or resistance to any one of diseases, insect infestation, and fungal infestation. In an alternative preferred embodiment, the quantitative trait is selected from amount of florets, amount of seeds, amount of empty seeds, amount of branching, weight of seeds, total weight of seeds and/or fill rate.

However, other types of parameters and/or combinations of the named parameters and/or other parameters may be possible, e.g. number and size of harvested organs per plant and per area; content of oil, starch and/or protein in harvested organs (e.g., seeds or vegetative parts of the plant); number of flowers (florets) per panicle or alternatively the number of flowers can be expressed as a ratio of number of filled seeds over number of primary panicles for one plant); or modified architecture (such as increase stalk diameter, thickness, branching or improvement of physical properties).

The apparatus furthermore may comprise a control system 190 which may be adapted to control and/or to drive the imaging system and/or transporter 130 and/or the conveyor belt systems 131, 132 and/or the image analysis device and/or the reader and/or the database and/or a power supply. The control system 190 may comprise a computer and electrical and/or signal connectors, preferably electrical lines and interfaces.

Preferably, the imaging system 120 is shielded from natural daylight. Light inside the imaging system 120 may be provided by a set of lamps (not shown) of which the intensity can be controlled.

Images 150 taken in the imaging system 120 can be processed on-line using imaging analysis software to extract information on the panicles and preferably, the processed data as well as the images get linked to a unique identifier and even more preferably, downloaded to a computer.

Figure 2:
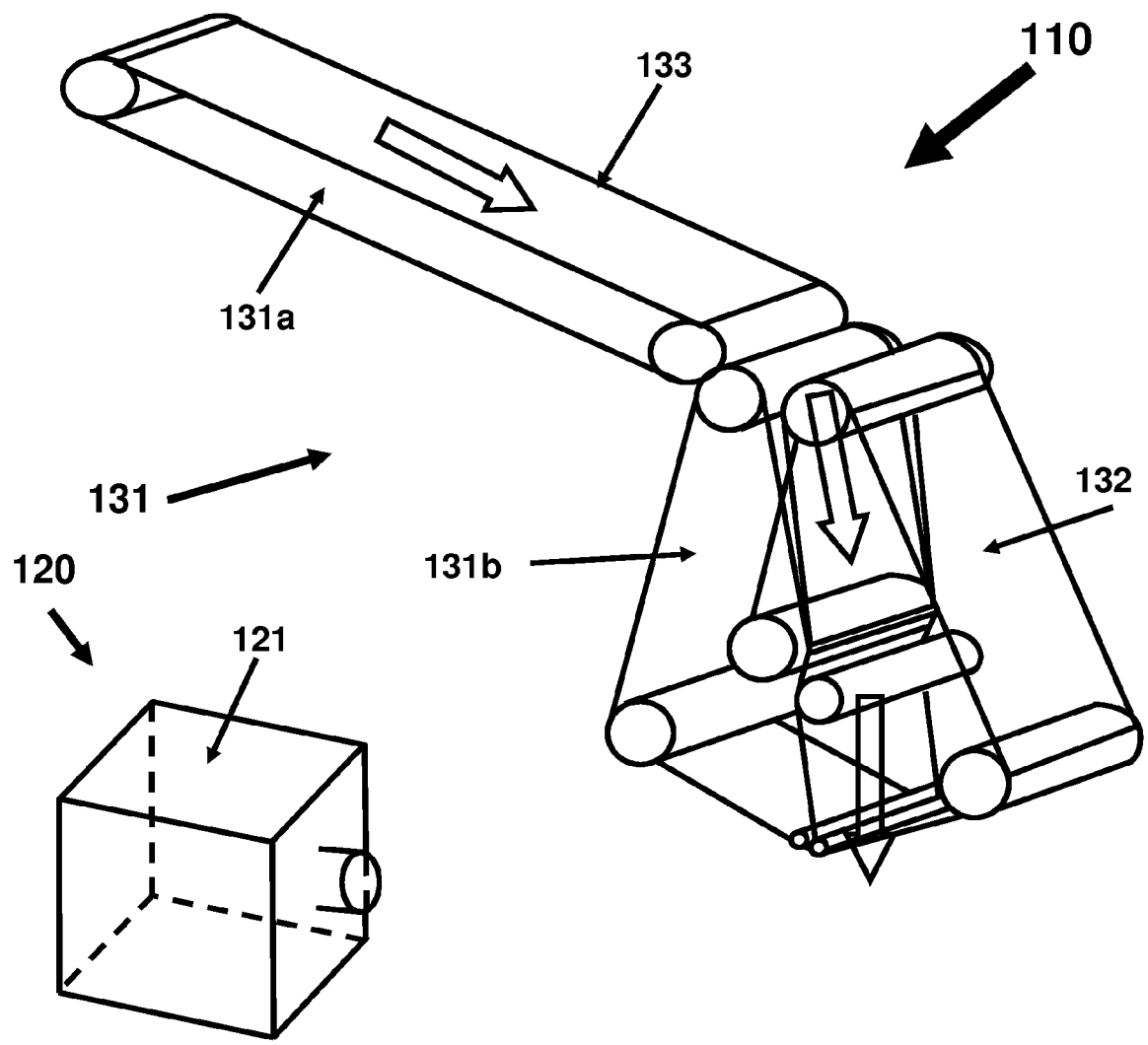
FIG. 2 is a schematic side view of one embodiment of another apparatus for high throughput imaging of cut panicles.

In a second exemplary embodiment, as shown in FIG. 2, the first conveyor belt system 131 has a free running zone 133. And the first conveyor belt system 131 comprises two conveyor belts 131*a* and 131*b*. In this case, the second conveyor belt system 132 is placed downstream of the free running zone 133 of the first conveyor belt system 131. A panicle (not shown, traject shown with arrows) is then placed on the free running zone 133 of this first conveyor belt system 131, preferably with the tip of the panicle first in the running direction of the first conveyor belt system 131. The panicle is then moved forward on said first conveyor belt system 131 towards the second conveyor belt system 132 and the panicle is then squeezed or gripped between both first and second conveyor belt systems 131, 132 downstream of said free running zone 133. At the end of the gripping conveyor systems 131, 132 the panicle is presented to the imaging system 120. As such, the panicle is hanging downward due to gravity forces. When the panicle is taken downward parallel to the direction of gravity, the panicle will be hanging completely straight due to gravity forces. The imaging system 120, which is preferably positioned such that it is imaging in a direction perpendicular to the moving direction of the panicle, acquires at least one image. Thereafter, the panicle is released from these gripping first and second conveyor belt systems 131, 132 into a collector bin (not shown). The phenotype is measured from the image by appropriate software.

If desired, algorithms may be used to evaluate the measured phenotype.

The imaging system 120 comprises a detector 121. In this example the detector 121 is a line scan digital camera.

All other modalities are as described for FIG. 1.

Figure 3:
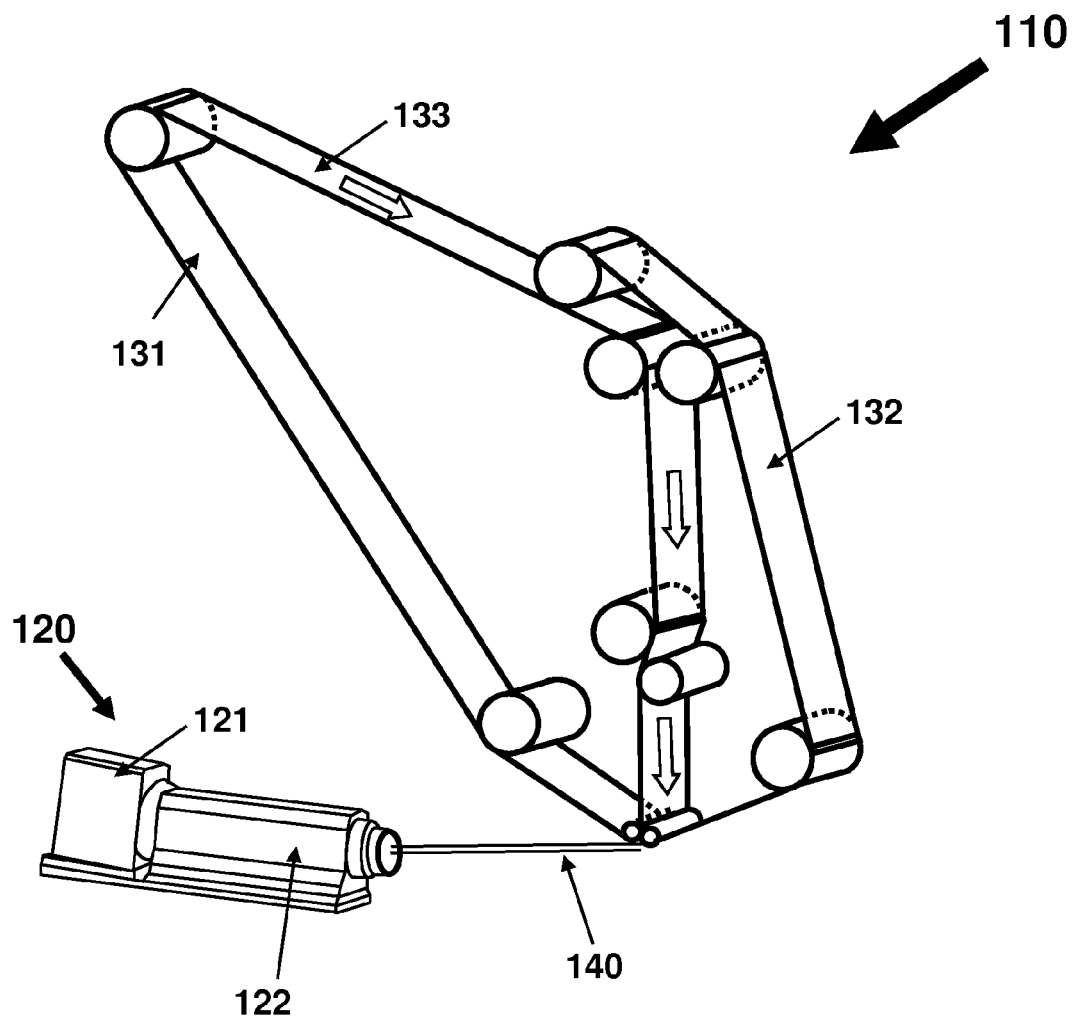
FIG. 3 is a schematic side view of one embodiment of another apparatus for high throughput imaging of cut panicles.

In a third exemplary embodiment, as shown in FIG. 3, the first conveyor belt system 131 has a free running zone 133. Also in this case, the second conveyor belt system 132 is placed downstream of the free running zone 133 of the first conveyor belt system 131. A panicle (not shown) is then placed on the free running zone 133 of this first conveyor belt system 131, preferably with the tip of the panicle first in the running direction of the first conveyor belt system 131. The panicle is then moved forward on said first conveyor belt system 131 towards the second conveyor belt system 132 and the panicle is then squeezed or gripped between both first and second conveyor belt systems 131, 132 downstream of said free running zone 133.

In this example, the first conveyor belt system 131 consists of one belt and also the second conveyor belt system 132 consists of one belt.

In the exemplary embodiment of FIG. 3 the imaging system 120 is shielded from natural daylight (not shown). Light inside the imaging system 120 may be provided by a set of lamps (not shown) of which the intensity can be controlled.

In this exemplary embodiment, the imaging system 120 comprises the following:
  at least one light source with suitable spectral composition in the near infrared range to direct electromagnetic radiation onto said panicle with light 140,
  at least one detector 121 with sensitivity in the near-infrared range;
  at least one spectrograph 122 composed of an optical dispersing element such as a grating or prism to split the light into many narrow, adjacent wavelength bands, said spectrograph 122 being placed before the detector;
  at least one suitable optical lens;
  computer hardware elements and connections to the different previous elements and
  dedicated software elements for driving signal outputs and inputs from and to the hardware elements, and automatically perform the different steps of the method described herein.

Such imaging is often referred to in literature as imaging spectroscopy, which is the simultaneous acquisition of spatially co-registered images in many spectrally contiguous bands. In the art, the wording "hyper spectral image cubes" are described as multichannel images being composed of many spectrally contiguous spectral bands of relatively narrow bandwidths (e.g., 1-10 nm), whereas, "multi-spectral" images are usually fewer (e.g., 5-10) bands of relatively large bandwidths (e.g., 70-400 nm), or fewer bands of relatively narrow bandwidths.

The imaging system at least comprises a detector 121. Such detector may be a hyperspectral camera. In another preferred embodiment, the imaging system comprises a multispectral camera.

Preferably, the imaging system described above comprises a spectrograph being tunable so that specific wavebands can be selected and transmitted to the camera in a predetermined sequence.

Figure 4:
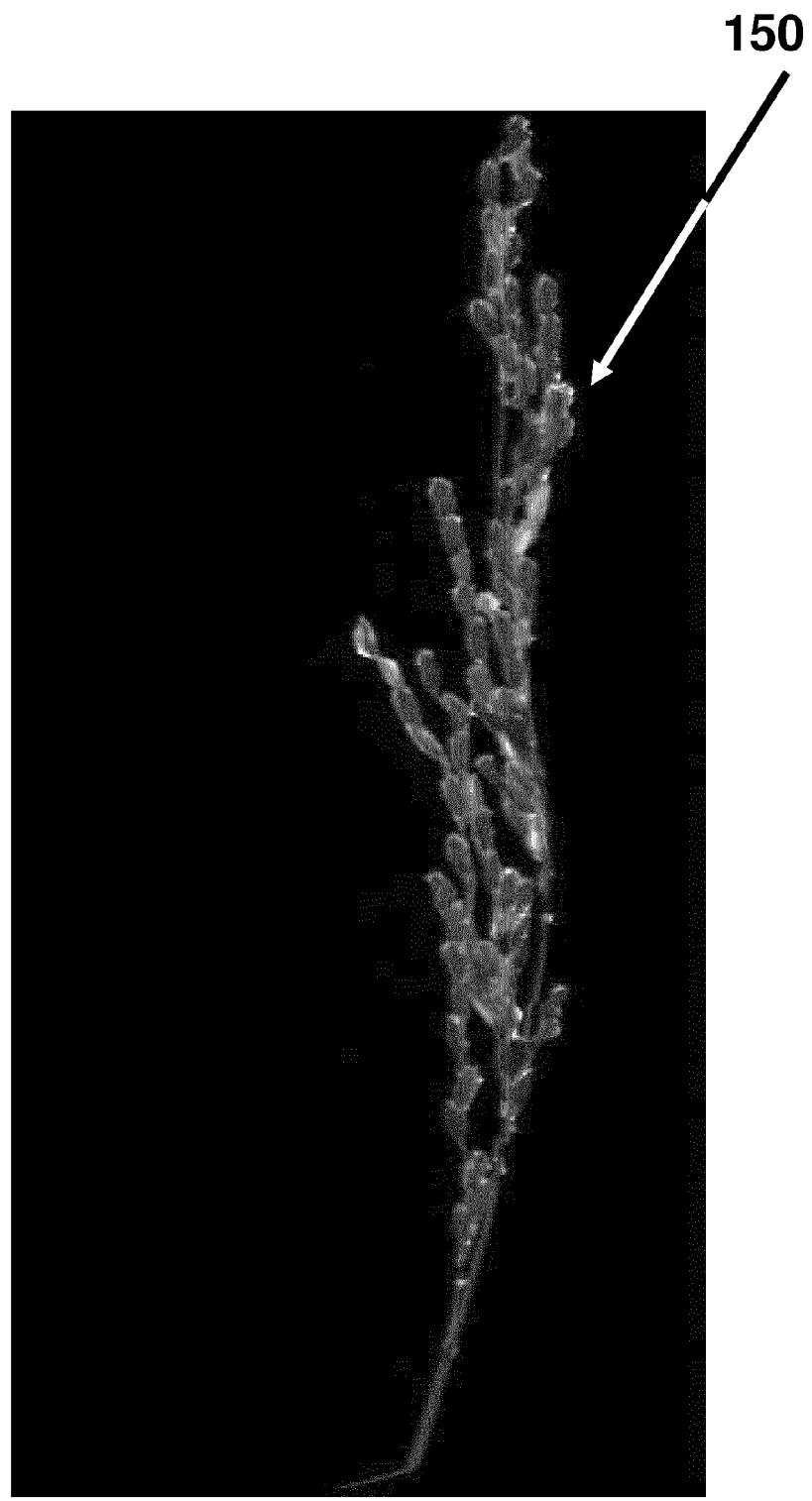
FIG. 4 shows a monochromatic image of a rice panicle obtained by the method and apparatus of the present invention.

FIG. 4 shows a monochromatic image which is a selection of one waveband in the 2 dimensional space from the hyperspectral image.

In an exemplary embodiment, the method according to the invention involves the following steps:
  first a first and second conveyor belt system and an imaging system are provided. The first and second conveyor belt systems run simultaneously and in the same direction. The second conveyor belt system is placed face-to-face with the first conveyor belt system such that said first and second conveyor belt systems perform a squeezing or gripping action.
  A panicle, which is cut from a plant, is provided.
  Identification of each panicle or group of panicles belonging to an individual plant being measured by means of unambiguous coding system. Ideally the coding system is of a type that can be read electronically, e.g. barcode, or transponder tag.
  Providing at least one panicle to the first and second conveyor belt system. The panicle is provided to the conveyor belt systems with the tip of the panicle first in the running direction of both conveyor belt systems. These first and second conveyor belt systems take the panicle downward. Preferably the panicle is taken to a position wherein the panicle axis is parallel to the gravity direction. In a preferred embodiment, the first and second conveyor belt systems end substantially simultaneously. In another preferred embodiment, one of the conveyor belt systems further assists the transportation of the panicle towards and/or in front of the imaging system. At the end of the gripping conveyor systems the panicle is presented to the imaging system. As such, the panicle is hanging freely due to gravity forces.
  Collection of digital images of individual plant panicles bearing seeds at the final maturity stage, when the seeds are normally harvested. One image of each individual panicle is collected by use of an imaging system, in this example a digital camera.
  Generation of seed size, seed count (amount), seed, amount of spikelets, panicle size, shape and branching pattern using appropriate software.
  Determination of the pixels belonging to the plant organs, as opposed to the non-plant background. This is achieved using standard image processing algorithms, such as intensity thresholding, in which the pixel values differing from predetermined background values are considered as belonging to the plant object.
  Determination of pixels belonging to the seeds, as opposed to the rest of the plant organs. This is achieved by standard image processing algorithms, such as morphological segmentation, in which objects are identified as seed or non-seed when their geometrical properties correspond to predefined specifications.
  Calculation of the metric properties per each individual object identified in the image, based on the combined properties of all individual pixels constituting each object. These properties include amongst other physical dimensions in the 2 dimensional space and amount of seeds.

In a further exemplary embodiment, the method of the invention involves the following steps:
  first a first and second conveyor belt system and an imaging system are provided. The first and second conveyor belt systems run simultaneously and in the same direction. The second conveyor belt system is placed face-to-face with the first conveyor belt system such that said first and second conveyor belt systems perform a squeezing or gripping action.

A panicle, which is cut from a plant, is provided.

Identification of each panicle or group of panicles belonging to an individual plant being measured by means of unambiguous coding system. Ideally the coding system is of a type that can be read electronically, e.g. barcode, or transponder tag.

Providing at least one panicle to the first and second conveyor belt system. The panicle is provided to the conveyor belt systems with the tip of the panicle first in the running direction of both conveyor belt systems. These first and second conveyor belt systems take the panicle downward. Preferably the panicle is taken to a position wherein the panicle axis is parallel to the gravity direction. In a preferred embodiment, the first and second conveyor belt systems end substantially simultaneously. In another preferred embodiment, one of the conveyor belt systems further assists the transportation of the panicle towards and/or in front of the imaging system. At the end of the gripping conveyor systems the panicle is presented to the imaging system comprising a detector. As such, the panicle is hanging freely due to gravity forces.

Collection of digital images of individual plant panicles bearing seeds at the final maturity stage, when the seeds are normally harvested. Many images of the same individual panicles are collected at many different narrow wavebands in the near infrared range of the light spectrum, namely between 900 and 1700 nanometers.

Generation of hyper-spectral image cube by alignment of the images recorded at the different wavelengths in order to generate a 3 dimensional image comprising 2 spatial dimensions (x, y) and 1 spectral dimension (z). From such images, a spectrum of light absorption for each pixel in the two-dimensional space can be generated.

Estimation of the amount of dry matter and basic chemical composition corresponding to each pixel, based on a customary predictive mathematical model combining the weighted contributions of the different wavelengths at each pixel.

Determination of the pixels belonging to the plant organs, as opposed to the non-plant background. This is achieved using standard image processing algorithms, such as intensity thresholding, in which the pixel values differing from predetermined background values are considered as belonging to the plant object.

Determination of pixels belonging to the seeds, as opposed to the rest of the plant organs. This is achieved by standard image processing algorithms, such as morphological segmentation, in which objects are identified as seed or non-seed when their geometrical properties correspond to predefined specifications.

Calculation of the metric properties per each individual object identified in the spectral image, based on the combined properties of all individual pixels constituting each object. These properties include: physical dimensions in the 2 dimensional space, estimated dry weight, and estimated basic chemical composition.

The invention claimed is:

1. An apparatus for high-throughput evaluation of inflorescence, seed and/or seed yield of a panicle, which apparatus comprises:
   an imaging system; and
   a transporter for supporting and moving said panicle to said imaging system;
   said transporter comprising two conveyor belt systems, said conveyor belt systems being placed face-to-face for gripping a panicle to be evaluated;
   wherein said imaging system comprises:
      at least one light source with suitable spectral composition in the near infrared range to direct electromagnetic radiation onto said panicle;
      at least one digital camera with sensitivity in the near-infrared range;
      at least one spectrograph comprising an optical dispersing element adapted to split the light into many narrow, adjacent wavelength bands, said spectrograph being placed before the camera;
      at least one optical lens;
      computer hardware elements and connections to the foregoing imaging system elements; and
      dedicated software elements for driving signal outputs and inputs from and to the hardware elements, and for automatically acquiring at least one spatially resolved image of a panicle and measuring a phenotype of said panicle from said image.

2. The apparatus of claim 1, wherein said imaging system comprises at least one detector.

3. The apparatus of claim 1, wherein:
   the imaging system is adapted to image said panicle at different wavelengths of electromagnetic radiation from the at least one light source, thereby obtaining images comprising pixels; and
   the software elements are adapted to:
      align said images recorded at different wavelengths on the basis of said pixels, thereby generating a 3-dimensional imaging cube, said 3-dimensional imaging cube comprising 2 spatial dimensions and 1 spectral dimension;
      use a customary predictive mathematical model combining the weighted contributions of the different wavelengths, thereby correlating the multispectral or hyperspectral imaging cube of said panicle to a phenotype; and
      measure the phenotype from said correlation.

4. A method for measuring inflorescence, seed and/or seed yield phenotype, the method comprising:
   measuring inflorescence, seed and/or seed yield phenotype of a panicle using the apparatus of claim 3.

5. The apparatus of claim 1, wherein said phenotype comprises one or more of a quantitative trait, a biochemical trait, and a morphological trait.

6. The apparatus of claim 5, wherein said phenotype comprises said biochemical trait, which is selected from the group comprising of oil composition, protein composition, carbohydrate composition, fiber composition, oil content, protein content, carbohydrate content, starch content, fiber content, dry weight, and water content.

7. The apparatus of claim 5, wherein said phenotype comprises said morphological trait, which is selected from the group comprising inflorescence architecture, endosperm size, germ size, seed shape, seed size, seed color, seed surface texture, seed weight, seed density, and seed integrity.

8. The apparatus of claim 7, wherein said morphological trait comprises said seed integrity, which is correlated to susceptibility or resistance to any one of diseases, insect infestation, and fungal infestation.

9. The apparatus of claim 5, wherein said phenotype comprises said quantitative trait, which is selected from the group comprising amount of florets, amount of seeds, amount of empty seeds, amount of branching, weight of seeds, total weight of seeds, and fill rate.

10. A method for measuring inflorescence, seed and/or seed yield phenotype, the method comprising:
 measuring inflorescence, seed and/or seed yield phenotype of a panicle using the apparatus of claim 1.

11. A method for analysis of stress resistance of plant specimens, the method comprising:
 analyzing stress resistance of a plant specimen using the apparatus of claim 1.

\* \* \* \* \*